United States Patent [19]

Amarasinghe

[11] Patent Number: 4,936,826
[45] Date of Patent: Jun. 26, 1990

[54] VENA CAVA WINDOW

[76] Inventor: Disamodha C. Amarasinghe, IMA Medical Center, 700 Independence Circle, Suite 2A, Virginia Beach, Va. 23455-6438

[21] Appl. No.: 261,736

[22] Filed: Oct. 24, 1988

[51] Int. Cl.$^5$ .......................................... A61M 31/00
[52] U.S. Cl. ................................ 604/52; 604/53; 604/175
[58] Field of Search .................. 604/174, 175, 52, 53, 604/43–45, 158, 270, 271, 272, 273, 96, 280

[56] References Cited

U.S. PATENT DOCUMENTS

| | | | |
|---|---|---|---|
| 4,392,855 | 7/1983 | Oreopoulos et al. | 604/175 |
| 4,406,656 | 9/1983 | Hattler et al. | 604/280 |
| 4,431,426 | 2/1984 | Groshong et al. | 604/280 |
| 4,437,857 | 3/1984 | Goldstein et al. | 604/53 |
| 4,583,968 | 4/1986 | Mahurkar | 604/43 |
| 4,626,240 | 12/1986 | Edelman et al. | 604/43 |
| 4,665,925 | 5/1987 | Millar | 128/663 |

Primary Examiner—John D. Yasko
Attorney, Agent, or Firm—Raymond L. Greene

[57] ABSTRACT

The invention is a combination device for long-term intravenous therapy comprising an outer sheath 11 and an inner catheter 15. The outer sheath 11 is permanently implanted in the patient allowing repeated or continuous access to the venous system. Inner catheter 15 is inserted into the outer sheath and comprises several conventional configurations such as single lumen, dual lumen, depending on the particular therapy. When therapy is complete, or when needed to avoid blockage by clotting or infection resulting from contamination, the inner catheter may be removed. When the inner catheter 15 is not in place, the sheath 11 is sealed at the proximal or skin-surface end by cap 16. The cap provides a flat, inconspicuous surface which may be covered with a small bandage. In this configuration, the patient is also protected from injury in that the likelihood of physical damage to protruding hardware is minimized. The present invention permits home therapy, including insertion and removal of catheters (using sterile techniques) by non-medical assistants.

13 Claims, 4 Drawing Sheets

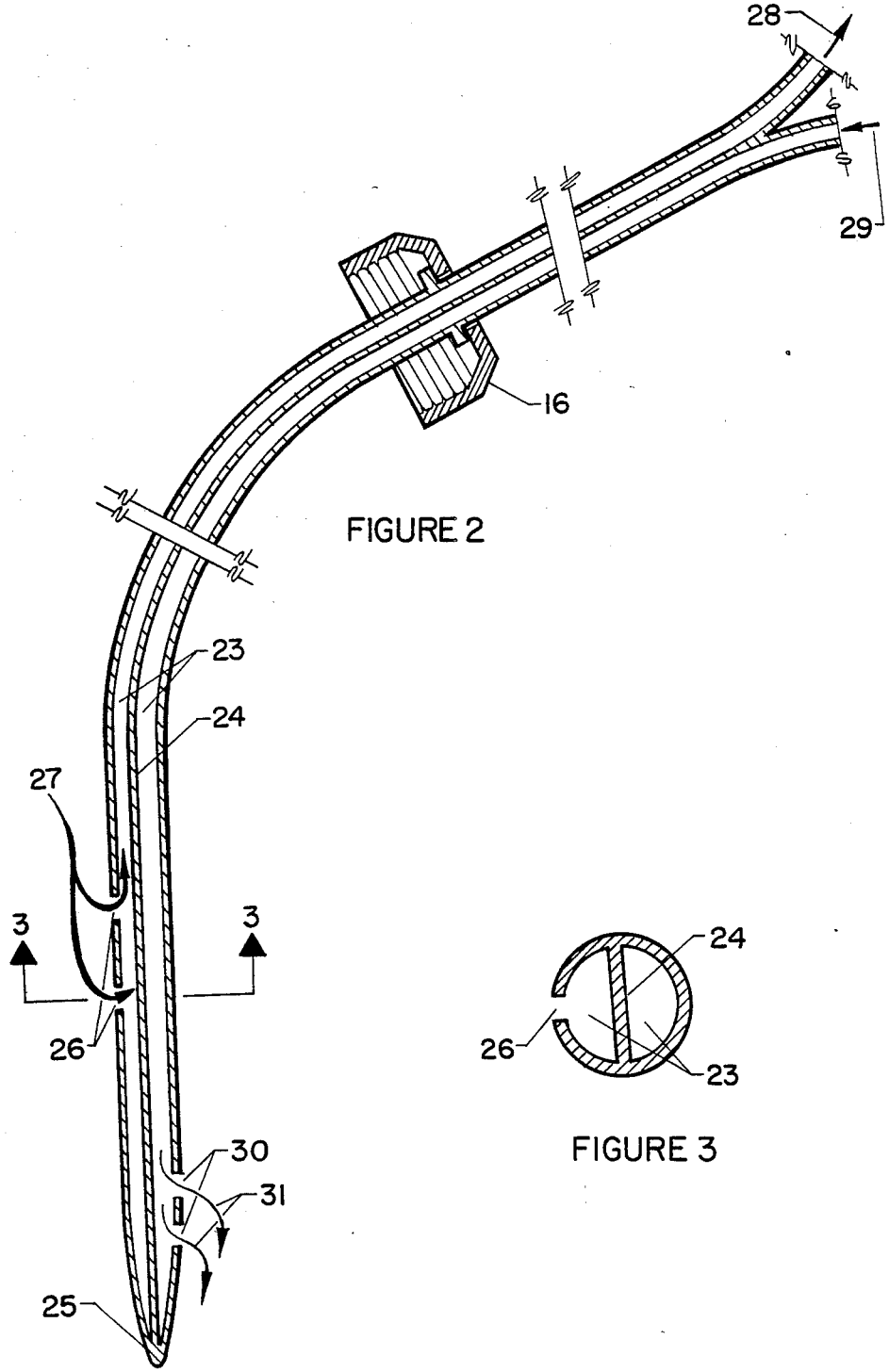

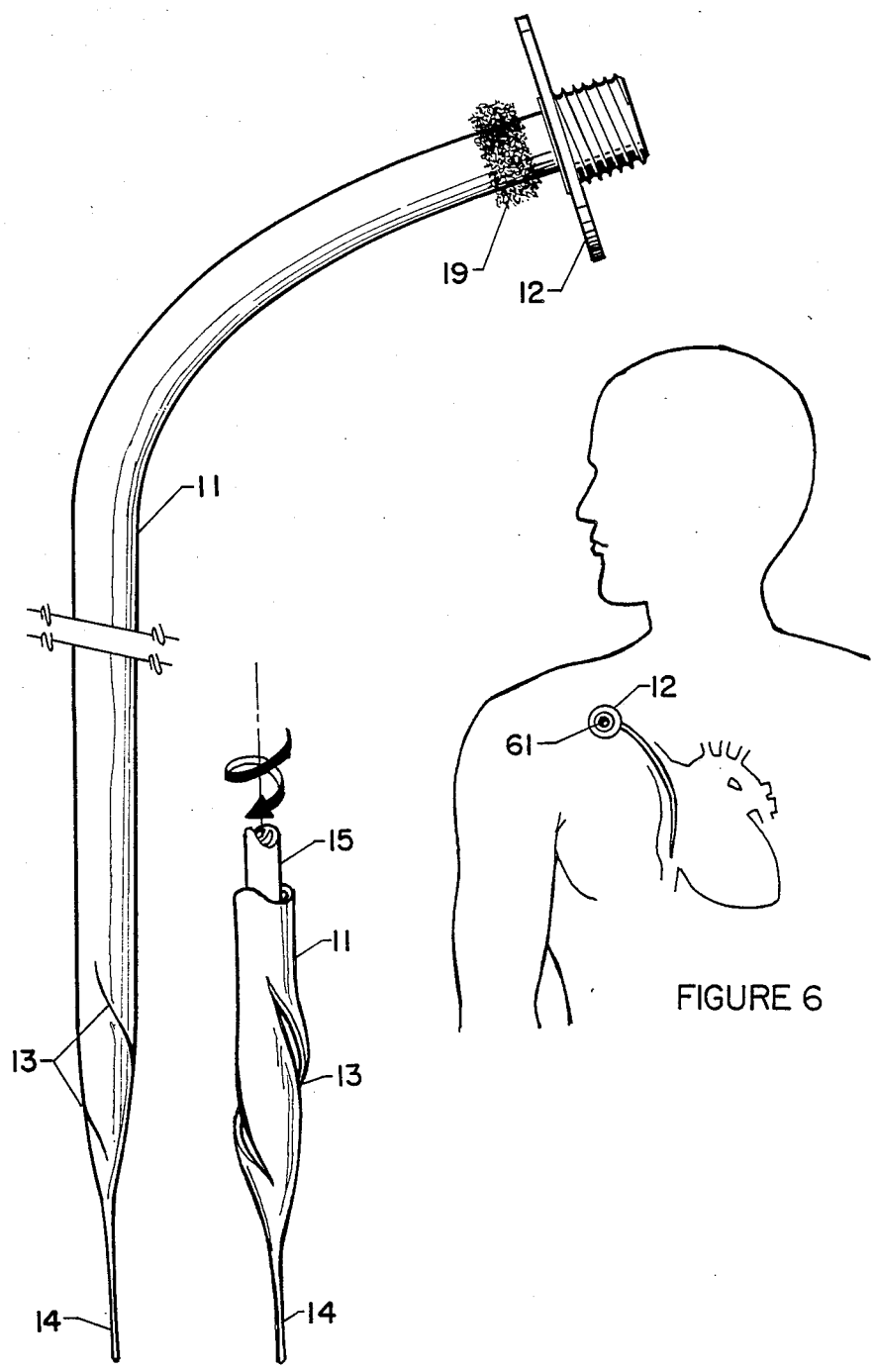

VENA CAVA WINDOW

BACKGROUND OF THE INVENTION

1. Field of the Invention

The invention relates to surgical instruments for withdrawing or introducing fluids into the body and more particularly to venous catheters.

2. Description of the Related Art

Development in the technology and instruments for intravenous therapy has been spurred by increasing needs for effective, long-term access to major veins and arteries. Increased use of hemodialysis, chemotherapy, hyperalimentation and the growing number of patients requiring frequent venous access, have resulted in a refinement of catheter devices for intravenous therapy. Commercially available devices include the Hickman Catheter (trademark), Raff Catheter (trademark) and Broviac Catheter (trademark). A more recent improvement over prior devices is the Groshong Catheter (trademark). Generally, these devices use a flexible catheter having single or multiple lumens. The cannula is inserted into the subclavian vein under the collarbone and led along the vein into the very large vein entering the heart, the vena cava superior. The access to the vena cava is required so that concentrated solutions being introduced into the patient will be rapidly diluted thereby avoiding the severe pain, vein inflammation and possible thrombosis associated with intravenous therapy using smaller veins located in the arms or legs. Hyperalimentation, or total nutritional support via intravenous transfer, precludes the use of small veins. Despite the resolution of thrombosis, and related difficulties, complications remain in the intravenous therapy procedures. The puncture at the proximal end or entrance point on the surface of the skin remains a primary source of infection. (Throughout this application, the word "proximal" will refer to the near end or surface end of the catheter or sheath where it normally attaches to the skin, and the word "distal" will refer to the far end, closer to the heart.) The hardware and tubing protruding from the patient's body not only provide a source of infection, but also expose the patient to potentially serious injuries in the event of an accidental dislodgment of the mechanism. Additionally, the hardware and associated protrusions are cosmetically unappealing and limit the patient's physical mobility.

Other problems with current catheters include clotting problems particularly where blood may clot in the distal end of the catheter, thereby requiring removal and replacement of the entire catheter. Some catheters must be flushed as often as every eight hours with an anticoagulant such as heparin. The major shortcomings of the current catheter hardware result from the permanent implantation of the catheter in the blood stream. Because of the permanent presence in the blood stream, a multitude of difficulties arise. The catheter itself is subject to clotting along the outer surface and clotting and obstruction within the lumen. Also, during intermittent intravenous therapy, such as that typical of home hyperalimentation, the entire internal surface of the catheter is filled with solution providing a "wet" environment likely to support fungal or bacterial growth. This risk is especially high where blood clots form around slit-style valves.

As the catheter is permanently implanted, cleaning by flushing with an anticoagulant solution is the only practical method of maintaining the patency of the device when flushing fails, surgical removal is the only alternative.

Further, dangers of fatal air embolism are present during surgical insertion and removal, and whenever the catheter is installed. Physical damage to the proximal end may dislodge the catheter or cause a break in the catheter with the potential result of an embolism. Similar physical damage may dislodge the catheter allowing it to migrate further into the vena cava. Finally, despite the permanent insertion of the catheter, replacement is necessary at frequent intervals to avoid infection, contamination and blockage by clotting. Accordingly, it is an object of the present invention to provide means to permit multiple, non-traumatic insertions and removals of intravascular catheters.

Another object of the present invention is to provide a positive mechanical valve for the distal end of a catheter assembly.

It is yet another object of the present invention to provide a dry environment for the catheter cannula.

Still another object of the present invention is to provide a catheter apparatus for intravenous therapy which will substantially reduce the risk of loss of blood and the risk of air embolism Yet another object of the present invention is to provide a catheter apparatus for intravenous therapy which will not require anticoagulant flushing.

A further object of the present invention is to provide a catheter apparatus for intravenous therapy which will substantially reduce the risk of infection It is still a further object of the present invention to provide a sheath-catheter combination which will allow ready removal of the catheter leaving the sheath in place to provide a repeated access for long term intravenous therapy.

It is another object of the present invention to provide a catheter entry means at the skin surface which is cosmetically and functionally designed to eliminate protruding tubing and hardware.

SUMMARY OF THE INVENTION

The invention is a sheath and inner catheter combination suitable for long term implants for intravascular therapy. The sheath is a curved or semi-flexible sleeve having a small attachment collar at the proximal end and a valve at the distal end. The collar attaches to the skin and holds the distal end of the sheath at the skin surface. The sheath is thereby secured in position in the vena cava using a skin attachment which is relatively flush and unobtrusive. The valve at the distal end, inside the vena cava, is closed whenever the inner catheter is not inserted. When the vena cave window is not in use, a small cap also closes the proximal end of the sheath at the skin surface and the entire assembly may be covered with a small bandaid-like bandage.

The inner catheter is supplied to the patient in a sealed, sterile package and is inserted into the sheath by removing the sheath cap and feeding the catheter into the sheath. Although sterile techniques are required, this operation can be accomplished during home therapy by a non-medical assistant.

During the last part of the insertion travel, the catheter opens a valve at the distal end of the sheath. At this point, the inner catheter has access to the blood stream for either returning blood or intravenous infusion. When therapy is complete, the inner catheter is withdrawn and discarded and the sheath is re-sealed. The patient in this manner can be afforded a full range of intravenous therapy outside the hospital while retaining full mobility and safety. The most common method in current use for hemodialysis involves the use of an arterio-venous fistula formed by synthetic graft of artery and vein. The present invention has the potential to completely change the current methods, thereby not only because providing dramatic reductions in cost, but also permitting out-patient, at-home, therapy.

BRIEF DESCRIPTION OF THE DRAWINGS

In the following drawing, the scale and clearances of the various tubes, sheaths, valves and other parts have been enlarged for clarity of construction. In the preferred embodiment, the outside diameter of the sheath is one to four millimeters depending on the specific use (chemotherapy, dialysis, etc.). The fit between the sheath and the catheter is snug. The outside diameter of the inner catheter is approximately one-half to one millimeter less than the inner diameter of the outer sheath. As a result, very little fluid or air space occurs between them. A more complete appreciation of the present invention and the many attendant advantages thereof will be readily apparent as the same becomes better understood by reference to the following description when considered in connection with the accompanying drawings wherein:

FIG. 1A is an exploded view in partial section of the combination of the invention showing the sheath with the inner catheter being inserted into position for intravascular therapy.

FIG. 2 is a longitudinal section of the inner catheter showing inlet and outlet ports.

FIG. 3 is a cross-sectional view showing a double lumen catheter with an entry port in one lumen.

FIG. 4 is a longitudinal view of the sheath depicting the valve arrangement at the distal end and the collar assembly at the proximal end.

FIG. 5 is a perspective view of the distal end of the sheath showing the operation of the spiral valve of the preferred embodiment.

FIG. 6 shows a schematic of the sheath implanted in a patient and extending through the subclavian into the vena cava.

DETAILED DESCRIPTION OF THE PREFERRED EMBODIMENT

Figures 1, 1B:
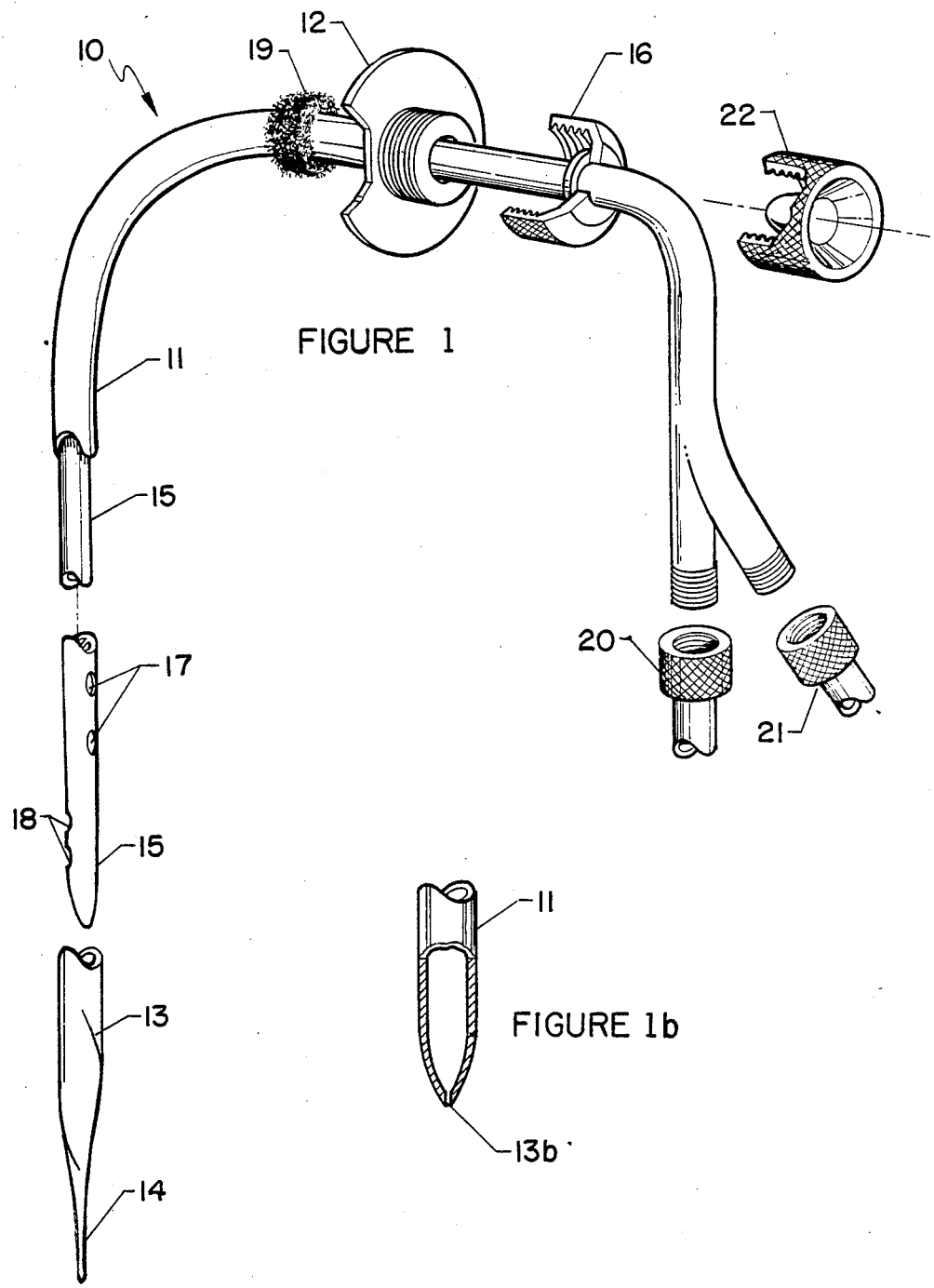
FIG. 1B is a cut-away view of an alternate embodiment of the sheath valve arrangement.

Referring now to FIG. 1, an exploded view of the combination sheath and catheter of the present invention, designated generally by the numeral 10, depicts the major elements thereof. The sheath 11 of the present invention has a retaining collar 12 at the proximal end and a spiral check valve 13 at the distal end. During initial insertion of the sheath, the rat-tail end 14 serves to facilitate leading of the sheath along the vein while avoiding injury to the vena cava or tributaries. (The rat-tail end also receives the distal end of the catheter 15 which presses rat-tail 14 downward thereby opening spiral valve 13.) Catheter 15 is inserted into sheath 11 by sliding it into the sheath until a threaded fitting reaches collar 12. At that point, catheter 15 is affixed to the outside of collar 12 by threaded fitting 16, completing the insertion of the catheter and opening spiral valve 13. An alternate embodiment using a straight slit flutter valve 13B is depicted in FIG. 1B wherein sheet 11 has an opening which is activated by the downward movement of the inner catheter and, in a similar manner to the action of the spiral valve, operates independent from any hydrostatic pressures.

In the preferred embodiment, inner catheter 15 has a dual lumen configuration with inlet ports 17 and outlet ports 18. Additionally, a synthetic cuff 19 is shown attached to sheath 15 near the proximal end. This cuff provides a surface which will seal through the growth of skin. The material for the synthetic cuff in the preferred embodiment is Dacron (trademark) fibers. Any material which will induce the growth of tissue can be substituted. Inner catheter 15 is further threadably attached to venous therapy devices, such as dialysis machines, by fittings 20 and 21. When inner catheter 15 is removed, cap 22 closes the proximal end of sheath 11.

Referring now to FIG. 2, a longitudinal section of the inner catheter shows the dual lumen 23 formed by septum 24 across the diameter of the cannula Distal end 25 is located in the superior vena cava with blood flowing downward past the distal end toward the heart. Inlet ports 26 withdraw blood for processing at an upstream position as depicted by arrows 27 for dialysis. Arrow 28 depicts the path of the withdrawn blood through the return lumen of the catheter. After processing, the blood is returned via the infusion lumen shown by arrow 29 and finally enters the blood stream through outlet ports 30 with arrows 31 showing the flow of processed blood. Threaded fitting 16 is shown at the upper end of the catheter where the connection between catheter and sheath is made.

Referring to FIG. 3, septum 24 divides the catheter into two lumens 23, one of which shows inlet port 26. Section 3-3 in FIG. 2 provides a reference for the cross-section shown in FIG. 3 which depicts the configuration of the catheter lumens at the inlet port.

Referring now to FIG. 4, a longitudinal view of the sheath 11 depicts the arrangement of the major elements thereof. Fiber disk 19 is located at the proximal end of the sheath immediately beneath collar 12. Rat tail 14, providing a shape suitable for leading the sheath into the vein, is located at the distal end with spiral valves 13 located adjacent to and just above the rat-tail. Treatment of the sheath and rat-tail to minimize infection may be accomplished as with any conventional catheter.

Operation of spiral valve 13 is shown in detail by reference to FIG. 5 where a perspective view of the distal end of sheath 11 with catheter 15 inserted is shown during valve operation. During the final few centimeters of insertion, catheter 15 presses into the distal end 14 of the sheath elongating and opening spiral valve 13. The preferred length of the spiral valve is approximately two to three centimeters allowing proper separation of the inlet and outlet ports on the catheter. FIG. 5 shows an exaggerated view of the spiral action of the present invention for purposes of illustration. The twisting action causes the slit valves to open allowing flow in and out. In the preferred embodiment, the spiral valve responds to both extension and twist to provide valve opening. The spiral valve is not independent of hydrostatic pressure and offers a higher sealing force than hydrostaticly-operated slit valve. Further, the valve does not restrict two-way flow once opened and therefore avoids difficulties encountered with the hydrostaticly-operated valves. Also, only a small segment of the catheter is exposed to the blood flow, the remainder being in the dry portion of the sheath. After use, in some cases, the catheter may be withdrawn from the sheath and discarded. When the next treatment is required a new catheter is inserted. There is no trauma to the patient. No surgery is required to re-insert a catheter inside the body. The venous trauma is eliminated and the amount of foreign material inside the vein is reduced. This configuration provides a great advantage to the patient in safety, mobility, comfort and appearance.

The improved appearance can be appreciated by reference to FIG. 6 wherein a front view of the collar assembly 12 is shown with the catheter removed and a threadably engaged plug 61 in place. In the sealed configuration as shown in this view, the sheath entrance presents a minimal profile. It can be covered with a small bandage and is completely invisible under any type of clothing.

Figure 7:
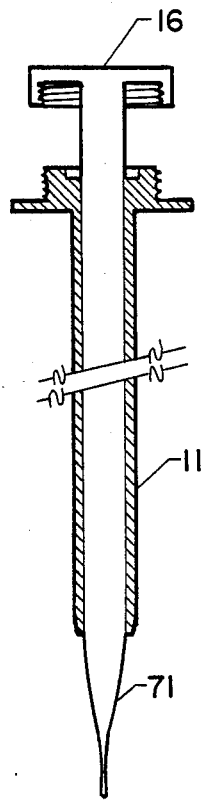
FIG. 7 is a longitudinal section of a miniaturized sheath and plug combination.
Figure 8:
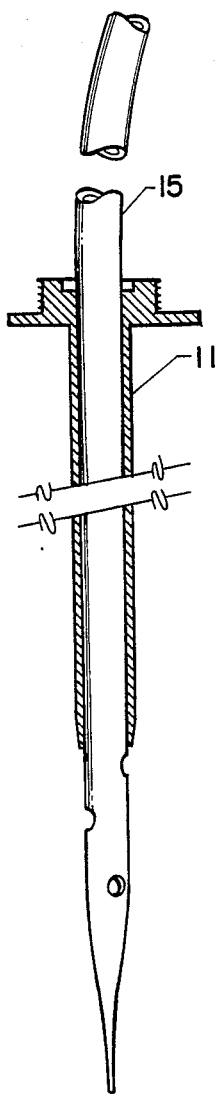
FIG. 8 depicts, in a longitudinal section, the miniaturized sheath with an alternate valve mechanism using inner catheter ports.

Referring now to FIG. 7, an alternate embodiment of the catheter-sheath combination is shown in section. A smaller version of the invention can be used for access to 1a minor vein in the arm or leg. In this embodiment sheath 11 is much small and shorter. No valve is located at the distal, the fluid flow being controlled by the insertion of an inner catheter with sidewall ports. After completion of intravascular therapy and removal of the inner catheter, an elongated plug 71 with cap 16 attached is inserted into the open sheath 11. By using this valving method a highly miniaturized version of the invention can be made while retaining the benefit of a removal catheter. FIG. 8 shows the insertion of the inner catheter 15 into miniature sheath 11. The snug fit maintains the dry environment inside the sheath.

Figure 9:
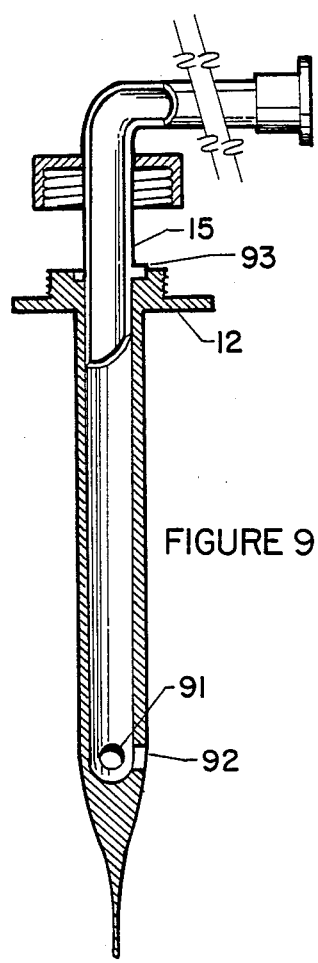
FIG. 9 discloses another valve mechanism using a rotating port device.
Figure 10:
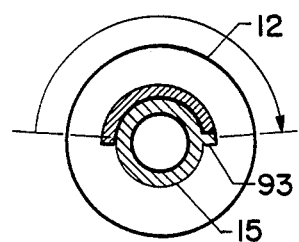
FIG. 10 shows a cross section of the rotation stop mechanism used with the rotating port in FIG. 9.

FIG. 9 shows another variation of the valving arrangement where fluid flow is controlled by rotation of inner catheter 15 such that catheter port 91 aligns with sheath port 92 to allow fluid transfer. To close the valve, stopping fluid flow, catheter port 91 is rotated away from sheath port 92. A rotation stop 93 is located at collar 12. The action of a rotation stop 93 is further shown in FIG. 10 wherein cap 12 is slotted so that rotation stop 93 can turn 180 degrees allowing inner catheter 15 to rotate thereby opening and closing the shuttle-port style valve at the distal end.

Although the intention has been described relative to a specific embodiment thereof, there are numerous variations and modifications that will be readily apparent to those skilled in the art in the light of the above teachings. It is therefore to be understood that, within the scope of the appended claims, the invention may be practiced other than as specifically described.

What is claimed as new and desired to be secured by Letter Patent of the United States is:

1. A combination device for intravenous therapy comprising:
    a sheath suitable for insertion into a vein having a proximal end to be located at the surface of the skin and a distal end to be located in a patient's vein;
    an inner catheter to be inserted inside said sheath capable of transferring fluids;
    means for attaching said sheath to said inner catheter;
    means for attaching said sheath to a skin surface;
    means for sealing the proximal end of said sheath; and
    means for controlling fluid flow located at the distal end of said sheath operable by mechanical movement of the inner catheter.

2. A combination device for intravenous therapy as in claim 1 wherein said sheath comprises a pre-curved cannula made of flexible, low-friction plastic material.

3. A combination device for intravenous therapy as in claim 1 wherein said catheter comprises a single lumen tube having a sealed distal end and a plurality of ports along the sidewalls of the catheter near the distal end.

4. A combination device for intravenous therapy as in claim 1 wherein said inner catheter is a dual lumen tube having, near the distal end, a plurality of inlet ports leading to a first lumen and a plurality of outlet ports leading from a second lumen, said groups of ports being spaced approximately ten centimeters apart with the outlet ports nearer to the distal end.

5. A combination device for intravenous therapy as in claim 1 wherein said means for attaching said sheath to an inner catheter comprises a male fitting on said sheath which threadably engages a female collar on said inner catheter.

6. A combination device for intravenous therapy as in claim 1 wherein said means for attaching the sheath to a skin surface comprises a polyester cuff suitable for attachment by growth of skin tissue.

7. A combination device for intravenous therapy as in claim 1 wherein said means for controlling fluid flow located at the distal end of said sheath is a spiral valve which can be opened by twisting and pressing longitudinally on the inside of the sheath distal end.

8. A combination device for intravenous therapy as in claim 1 wherein said means for controlling fluid flow located at the distal end of the sheath comprises a mechanically-operated flutter valve.

9. A combination device for intravenous therapy as in claim 1 wherein said means for controlling fluid flow at the distal end of said sheath comprises a shuttle valve operable by rotating the inner catheter within the outer sheath such that ports in both catheter and sheath are aligned.

10. A combination device for intravenous therapy as in claim 1 wherein said means for sealing the proximal end of said sheath is an obturator having a flat cap such the entry point on the body of the patient has no protruding parts.

11. A method for long-term intravenous therapy comprising the steps of:
    providing a permanent access to a vein;
    inserting a temporary access to the vein through said permanent access;
    through said permanent access;
    transferring fluids to and from the bloodstream through said temporary access;
    removing said temporary access; and sealing said permanent access.

12. A method for long-term intravenous therapy as in claim 11 wherein said step of providing a permanent access to a vein comprises surgical implanting a sheath having means for sealing both distal and proximal ends.

13. A method for long-term as in claim 11 wherein said step of inserting a temporary access to the vein comprises inserting a removable catheter in said permanent access.

* * * * *